United States Patent
May et al.

(10) Patent No.: US 8,710,834 B2
(45) Date of Patent: Apr. 29, 2014

(54) DRIVE COIL, MEASUREMENT PROBE COMPRISING THE DRIVE COIL AND METHODS UTILIZING THE MEASUREMENT PROBE

(75) Inventors: Andrzej Michal May, Schenectady, NY (US); Waseem Ibrahim Faidi, Schenectady, NY (US); Changting Wang, Niskayuna, NY (US); Nilesh Tralshawala, Rexford, NY (US); Aparna Chakrapani Sheila-Vadde, Bangalore (IN); Mandar Diwakar Godbole, Bangalore (IN); Jamie Thomas Livingston, Simpsonville, SC (US); Steven Haines Olson, Greer, SC (US); Howard Daniel Driver, Greer, SC (US)

(73) Assignee: General Electric Company, Niskayuna, NY (US)

( * ) Notice: Subject to any disclaimer, the term of this patent is extended or adjusted under 35 U.S.C. 154(b) by 55 days.

(21) Appl. No.: 12/870,804

(22) Filed: Aug. 28, 2010

(65) Prior Publication Data

US 2010/0321012 A1    Dec. 23, 2010

Related U.S. Application Data

(63) Continuation-in-part of application No. 12/325,179, filed on Nov. 29, 2008.

(51) Int. Cl.
*G01N 27/82* (2006.01)

(52) U.S. Cl.
USPC .......................................... 324/240; 324/228

(58) Field of Classification Search
USPC .................................................. 324/228, 240
See application file for complete search history.

(56) References Cited

U.S. PATENT DOCUMENTS

| | | | |
|---|---|---|---|
| 4,944,185 A | | 7/1990 | Clark et al. |
| 5,833,795 A | * | 11/1998 | Smith et al. ................. 156/272.4 |
| 6,586,930 B1 | * | 7/2003 | Kumar et al. ................. 324/225 |
| 7,250,763 B2 | * | 7/2007 | Mikhaltsevitch et al. .... 324/318 |
| 7,486,168 B2 | * | 2/2009 | Kim .............................. 336/200 |
| 2008/0174306 A1 | | 7/2008 | Brady |
| 2010/0005896 A1 | | 1/2010 | Miller et al. |
| 2010/0134098 A1 | | 6/2010 | Faidi et al. |

FOREIGN PATENT DOCUMENTS

| | | |
|---|---|---|
| DE | 3624808 A1 | 1/1988 |
| WO | 2009155000 A2 | 12/2009 |

OTHER PUBLICATIONS

Rudakov et al., "Improvement of the uniformity of the RF field generated by the helical surface coil of a Nuclear-Quadrupole-Resonance spectrometer", Electronics and radio engineering, Jun. 8, 2000.*

Clark JR., et al., "Tagged Adhesives for improved electromagnetic inspection", Materials Evaluation, 1990, pp. 60-64, vol. 48, No. 1.

Search Report and Written Opinion from corresponding EP Application No. 11176935.2-1240 dated Aug. 16, 2012.

* cited by examiner

*Primary Examiner* — Reena Aurora
(74) *Attorney, Agent, or Firm* — Ann M. Agosti

(57) ABSTRACT

The invention provides a drive coil and measurement probe comprising the drive coil. The measurement probes can be used, for example, in in-situ, non-destructive testing methods, also provided herein.

8 Claims, 12 Drawing Sheets

US 8,710,834 B2

DRIVE COIL, MEASUREMENT PROBE COMPRISING THE DRIVE COIL AND METHODS UTILIZING THE MEASUREMENT PROBE

BACKGROUND

The subject matter disclosed herein relates generally to composite systems, articles incorporating the composite systems, and methods for the in-situ non-destructive testing of the composite systems.

In many, if not all, manufacturing industries, the goods manufactured and the methods of manufacturing them are often impacted by the costs associated with parts and the shipping thereof. For example, in many industries, it may be desirable to produce parts on as large a scale as possible, e.g., pipelines for drilling applications, or blades for wind turbines, but yet doing so would present perhaps insurmountable shipping challenges or costs. On the other hand, manufacturing parts for such applications on a smaller scale then presents the challenge of having to assemble them in the field, with the difficulties attendant therewith, including at least the possibility of failure of any bonds formed in the assembly of the finished product.

Many physical methods of bonding may be preferable for forming such bonds from a strength, integrity and longevity perspective, but can present unwanted cost for the parts themselves as well as their shipping costs. And, physical bonding methods are not infallible.

Chemical bonding methods can prove advantageous in those applications where physical bonding methods prove suboptimal. However, chemical bonds may, in general, be less reliable, and so may require thorough nondestructive evaluations prior to utilization of articles incorporating the bonds. In the applications wherein assembly and chemical bonding occurs in the field, nondestructive assessment of the strength and/or integrity of the bond can be very difficult. Furthermore, conventional methods for doing so are generally time-consuming or otherwise costly, often requiring the utilization of highly-skilled experts in nondestructive testing (NDT). In certain applications, the materials being bonded can interfere with conventional NDT methods. Further, because many conventional NDT methods are not suitable for in-situ testing, real-time correction of any detected anomalies is not a possibility and so the use of NDT is not feasible during process development, manufacturing and joint assembly.

It would therefore be desirable to provide chemical-bonding systems capable of being effectively interrogated by means useful in a field situation, so that their integrity can be evaluated in-situ. The ability to conduct the evaluation in-situ (e.g., during application or curing of the resin) provides the opportunity to implement real-time correction strategies or to assess bond integrity during use. Such systems would provide additional advantages over conventional systems if expert implementation was not required, and/or they were suitable for use with a wide variety of materials typically contraindicated for NDT methods.

BRIEF DESCRIPTION

In a first aspect, the present invention provides a drive coil having a current density that monotonically increases from the center of the coil to an outer edge of the coil.

In a second aspect, the present invention provides a measurement probe. The measurement probe comprises a drive coil having a current density that monotonically increases from the center of the coil to an outer edge of the coil and a sensor.

A method for conducting nondestructive testing of a composite system is provided in a third aspect. More specifically, the method comprises providing a composite system comprising a curable resin further comprising at least one plurality of detectable particles as well as an article. At least one measurement probe is also provided and comprises a drive coil having a current density that monotonically increases from the center of the coil to an outer edge of the coil and a sensor. The measurement probe is capable of detecting the plurality of detectable particles within the composite system. The composite system is operatively disposed relative to the article and the sensor used to detect the detectable particles within the composite system.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
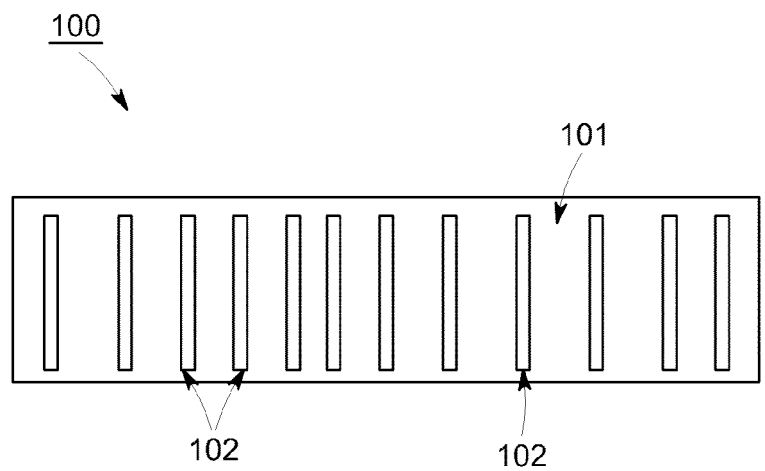
FIG. 1 is a cross-sectional view of an article incorporating composite system according to one embodiment of the present invention.

Unless defined otherwise, technical and scientific terms used herein have the same meaning as is commonly understood by one of skill in the art to which this invention belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation. If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). The modifier "about" used in connection with a quantity is inclusive of the stated value and has the meaning dictated by the context (e.g., includes the degree of error associated with measurement of the particular quantity).

In one aspect, the invention is directed to a composite system comprising a curable resin further comprising at least one plurality of detectable particles. Examples of curable resins include those that can be incorporated into or with other objects or articles, including for example, adhesives, sealants, caulks, gap-filling materials, coatings, conforming wraps and the like.

Suitable curable resins thus include thermoplastic polymeric compositions including polystyrene, polyethylene terephthalate, polymethylmethacrylate, polyethylene, polypropylene, polyvinylacetate, polyamide, polyvinyl chloride, polyacrylonitrile, polyesters, polyvinyl chloride, polyethylene naphthalate, polyether ketone, polysulfone, polycarbonate, and copolymers thereof. Other useful thermoplastics include engineering thermoplastics and thermoplastic elastomers. If a thermoplastic polymeric composition is desirably used as the curable resin, the thermoplastic resin can be combined with the plurality of detectable particles by heating the thermoplastic resin above its melting point or glass transition temperature until a suitable viscosity is reached, adding the plurality of detectable particles, blending, and then allowed the composite system to cool.

One example of a class of curable resins advantageously utilized in the present composite systems comprises adhesive and pre-adhesive compositions. Composite systems employing these curable resins may advantageously be dispensed, and the particles therein interrogated/detected during dispensation, polymerization or cross-linking, or afterward during use.

Adhesive compositions particularly well suited for use in the present invention include crosslinked thermosetting systems such as polyesters, vinyl-esters epoxies (including acid, base and addition cured epoxies), polyurethanes, silicone resins, acrylate polymers, polysiloxanes, polyorganosiloxanes, and phenolics, as well as blends or hybrids of any of these.

Useful hot melt adhesives include various polyolefins polyesters, polyamides, polycarbonates, polyurethanes, polyvinylacetates, higher molecular weight waxes, and related copolymers and blends. Additional suitable adhesives include those formed into films or tapes, including those that are pressure sensitive at any point in use.

Structural adhesives, including epoxy resins, may be particularly useful in the present composite systems. Structural adhesives are used in a variety manufacturing situations in bonding applications to reduce the need for welding, to reduce noise vibration harshness characteristics, or to increase the overall stiffness of the article.

Structural adhesives are typically prepared by reacting two or more pre-polymeric reagents with each other to form an intermediate, or B-stage resin, which is subsequently further cured to form the final product. In these embodiments, the detectable property of the particles can be monitored to provide an indication of whether the components were mixed in the proper ratio. In such embodiments, each component of the adhesive may comprise a plurality of detectable particles and the corresponding detectable property of each monitored to provide a similar indication, and such measurement used, e.g., to adjust the amount of each component being applied, if need be. Preferred structural adhesives for use in the present composite systems include polyesters, methyl methacrylates, and the like.

The curable resin may contain various additives designed to enhance the properties of the resin before or after curing, including reactive and nonreactive diluents, plasticizers, toughening agents and coupling agents. Other materials, which can be added to the composition, include thixotropic agents to provide flow control (e.g., fumed silica) pigments, fillers (e.g., talc, calcium carbonate, silica, magnesium, calcium sulfate, etc.) clays, glass, and ceramic particles (e.g., beads, bubbles and fibers) and reinforcing materials (e.g., organic and inorganic fibers and granular or spherical particles).

The curable resin further comprises at least plurality of detectable particles. Desirably, the particles comprise one or more material properties distinguishable from the same material property(ies) of the resin system, i.e., the material property of the particles may be different from that of the resin system, whether in a latent state or in an energized state, or the material property may not be exhibited by the resin system so that the property of the particles is distinguishable in the absence of the property of the resin system. Examples of material properties expected to differ between a resin system and that of the detectable particles will vary depending upon the composition of the particles, but will likely include at least magnetic permeability, dielectric constant, electric conductivity, thermal conductivity, density, or optical transmission.

Preferably, the particles utilized will have a property distinguishable from that of the resin system when monitored in situ, i.e., when the resin system is applied, as it is curing, or during use of an article into which the composite system is incorporated.

The particles may be comprised of any material, or combination of materials, that has at least one property detectable within the composite system. Desirably, the particles will be substantially chemically inert in the chosen curable resin under the relevant conditions and be stable with respect to degradation and leaching. Suitable particle materials will depend upon the curable resin selected for use in the composite system, and the property desirably measured. Examples of materials suitably detected by dielectric constant measurements include, but are not limited to, epoxies, glass and ceramics. Examples of materials suitably detected by electric conductivity measurements include, but are not limited to, metals (such as copper, aluminum and silver), metal alloys and metal compounds, such as carbides, oxides, nitrides, silicides, and quaternary ammonium salts. Examples of materials suitably detected by thermal conductivity measurements include, but are not limited to, metals (such as copper, aluminum, steel, sliver), glass, carbon, and ceramics. Examples of materials suitably detected by density measurements include, but are not limited to, glass, ceramics, metals, lead oxides, and silicas. Examples of materials suitably detected by nuclear quadruple resonance measurements include, but are not limited to, certain compounds based on copper, titanium, nitrogen, chlorine etc. Examples of materials suitably detected by piezoelectric conductivity measurements include, but are not limited to, piezoelectric ceramics, such as lead zirconium titanate (PZT), quartz, and polyvinylidene fluoride (PVDF). Examples of materials suitably detected by optical methods include, but are not limited to, metals, carbon, titanium oxide, and ceramics. The particles may of course, comprise a material having more than one property distinguishable from the curable resin, and one example of a material have at least two properties likely to be distinguishable from most curable resins is steel, which is both electrically conductive and ferromagnetic.

Because of their generally low cost and ready availability, magnetic materials, including ferromagnetic and ferrimagnetic materials, may advantageously be utilized in certain embodiments of the invention. For example, particles suitably detected via magnetic permeability methods may typically comprise ferromagnetic, or ferrite materials, as well as mineral oxides of magnetite, maghemite, jacobsite, trevorite, and magnesio ferrite, sulfides of pyrrhotite and greigite, and the metals/alloys of iron, nickel, cobalt, awaruite, and wairauite. Of these, ferromagnetic or ferrite materials are most readily available and economically attractive and are thus utilized in many embodiments of the invention.

The particles may comprise combinations of two or more materials, i.e., the particles may comprise coated, or otherwise surface treated, materials or may comprise composite materials. The only criteria is that, whatever the material(s) selected, and in whatever format selected, that the particles have at least one property distinguishable from that of the curable resin.

In certain embodiments of the invention, the particles may be selected, designed, and/or treated such that enhanced mechanical or chemical properties of the curable resin are obtained. Examples of particles expected to be so capable include, but not limited to, magnetic nano-particles with designed geometries, magnetic, and/or mechanical properties. If desired, the particles may further be treated with, e.g., silane or other coupling agent, to enhance the bonding of the particles to the curable resin.

If desirably coated, either the coating, particles or both, may comprise the detectable property. If present, coating may have an average thickness of between about 0.1 nanometers (nm) to about 500 nm, or about 0.5 nm to about 250 nm or from about 1 nm to about 100 nm, and all subranges therebetween. Further, the coating can, but need not, cover the entire surface of one or substantially all of the particle(s), and multiple coatings can be provided in overlapping layers, or as substantially discrete islands on the surface(s) of the particle(s).

If the detectable property is desirably provided in a coating, the particles themselves may be relatively inert, and may typically be comprised of materials typically used as pigments, reinforcing agents, rheology modifiers, density control agents or other additives in curable resins. Examples of particles comprising inert materials include, but are not limited to, glass bubbles, glass beads, glass fibers, fumed silica particles, fused silica particles, mica flakes, single- and multi-component polymeric particles and combinations thereof.

The use of the term 'particle' is not meant to indicate a particular required form or shape, and the particles may be in any suitable form that may be incorporated into the composite system chosen. Desirably, the particles chosen, and the format thereof will not detrimentally impact the material properties of the resin. Generally speaking, the particles may be any of a variety of shapes, including substantially spherical, elongated, or flat shapes and the shape may be selected to impart desired flow properties to the corresponding composite system given a selected concentration of detectable particles within the composite system.

Suitable particles are expected to have an average largest dimension of from about 1 Å (0.1 nm) to about 5000 Å (500 nm), or from about 10 Å (1 nm) to about 1000 Å (100 nm), or even from about 100 Å (10 nm) to about 500 Å (50 nm) and all subranges therebetween. In certain embodiments, the particles will desirably be ground, and in these embodiments are expected to have an average largest dimension of at least about 5 microns (5000 nm). Mixtures of particles sizes may also be utilized, and may assist in the detectability of the property or the uniformity of its expression within the resin system, and/or allow for optimized dispersion of the particles within the curable or cured resin.

Further, the detectable particles may be provided in any concentration so long as whatever the concentration utilized, it does not substantially interfere with the performance of the curable resin. In those embodiments wherein the curable resin comprises detectable functional groups, no detectable particles need be included, and composite systems with 0% detectable particles are considered to be within the scope of the invention.

Suitable particle loading or particle density will depend upon the particles utilized, and the distinguishable property to be measured. Generally speaking, particle density within the resin should not be such that the properties of the resin are substantially negatively impacted, and practically speaking, need not be more than that required to provide the property to be detected at a detectable level. Suitable detectable particle volume fractions are expected to range from about 0.001% to about 80% by weight (wt %), or from about 0.01 wt % to about 50 wt %, or even from about 0.1 wt % to about 10 wt %, and all subranges therebetween, based upon the total weight of the composite system. In those embodiments of the invention wherein the detectable particles are magnetic, particle volume fractions of under 1% may be sufficient to elicit a detectable response. And although combinations of the plurality of detectable particles and functional groups within the curable resin may be utilized as the detectable component, certain functional groups may provide a detectable response on their own, and in such embodiments, the composite system need not include any detectable particles.

Utilizing a particle density that approximates that of the liquid resin material may help achieve the proper buoyancy so that separation of particles does not ensue, or, a mixture of characterized particle sizes, including but not limited to nanoscale particles, may be used to allow for buoyant suspension optimization of particles in the resin and for an optimum shelf life of the composite system. The particles may also be treated with a density modifier to ensure optimal dispersion. For example, a wax coating can be added to a magnetic particle to achieve an overall density the same as, e.g., an epoxy, to achieve a uniform and non-separating suspension of the magnetic particles in the composite system.

The present composite system may advantageously be incorporated into an article. Any article desirably having a detectable property may benefit from incorporation of the composite system. Also, articles desirably assembled in the field may desirably be assembled to incorporate the present composite system and tested by the present method, since both provide the advantage of real-time monitoring and being amenable to testing by non-NDT experts.

Examples of articles desirably having the composite systems advantageously incorporated therein may include articles comprising a plurality of fibers, or articles incorporating one or more parts desirably having a detectable component operatively disposed relative thereto. That is, the composite system may be incorporated into a composite article, i.e., an article comprising fibers disposed within a matrix of the cured composite system. Such an article is shown in FIG. 1. More particularly, FIG. 1 shows article 100, with a matrix 101 comprising the composite system with fibers 102 disposed therein. Although fibers 102 are shown being similarly oriented and relatively evenly dispersed, this need not be the case, and any arrangement of fibers 102 within matrix 101 is considered to be within the scope of the present invention.

Alternatively, the composite system may be utilized to provide an article comprising two parts bonded together, or multiple parts desirably provided as a laminate. One embodiment of such an article is shown in FIG. 2, wherein article 200, comprises first part 203, and second part 204 with composite system 201 operatively disposed therebetween.

Figure 2:
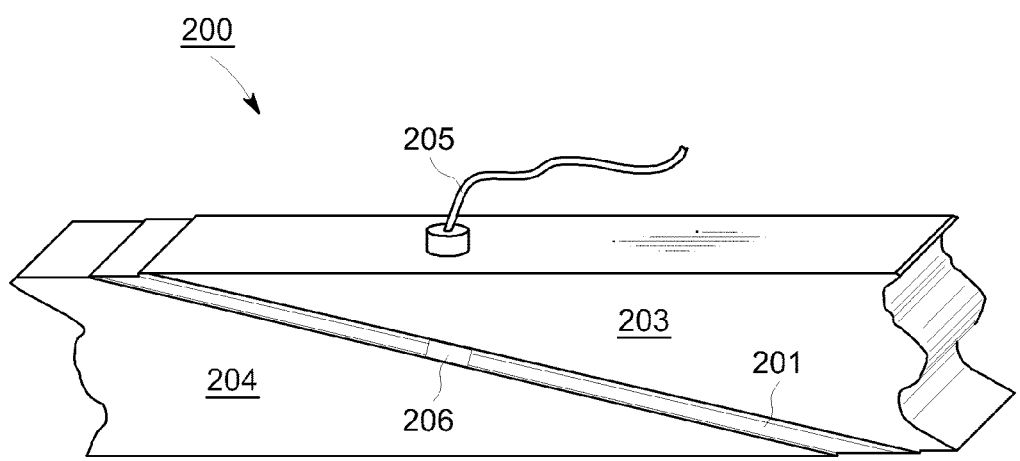
FIG. 2 is a is a cross-sectional view of an article incorporating composite system according to one embodiment of the present invention.

Whatever the article, the fibers (e.g., fibers 102 as shown in FIG. 1) or parts (e.g., parts 203 and 204 as shown in FIG. 2) thereof may advantageously comprise conductive material, such as carbon or carbon composites. Although articles comprising such materials can be difficult to test when bonded with conventional adhesives and/or tested by conventional methods, they are readily incorporated into the present articles, and in fact, can be utilized in some embodiments to enhance the measured signal provided by the detectable particles.

More specifically, and as but one example, in those embodiments of the invention wherein the detectable particles comprise ferrite powder and the curable resin comprises an adhesive, the article may comprise one or more electrically conducting materials which may enhance the measured eddy current signal generated due to the presence of the ferrite powder. This result is surprising and unexpected since electrically conductive material, usually acts as a shield and thus may typically decrease the eddy current measurement sensitivity. As those of ordinary skill in the art are aware, in these embodiments of the invention, the conductivity of the articles, the magnetic permeability of the composite system to be inspected, the eddy current sensor conditions, such as size and operating frequency, can all be utilized and adjusted in order to enhance the measurement sensitivity.

The present composite system is advantageously utilized in a nondestructive testing method, and such a method is also provided herein. Such testing can be used to determine a variety of properties of the composite system once incorporated relative to an article, including thickness, integrity, orientation, and continuity. Similarly, a map can be obtained indicating the location of the composite system.

As but one particular example, in the case when the curable resin comprises a structural adhesive forming a bond to join to parts of an article together, the properties of the bond line can be examined. Interrogation of the detectable particles within the curable resin, and thus, composite system, can be utilized to quantify the amount of detectable particles within a composite system, which in turn, may be used to determine, e.g., whether the proper amounts of each part of a two part adhesive have been combined. If the composite system comprising the detectable particles is moving, information obtained from the detectable particles can also be utilized to determine the flow and rate of deposition of the composite system. If the composite system is fixed, interrogation of the detectable particles may provide information on the distribution of the composite system throughout the article, within the bond space, etc.

In certain embodiments of the invention, measurements of the detectable particles may advantageously used as an indicator of stress in the curable resin or composite system. The level of stress, in turn, can be used, e.g., to determine the degree of cure of an adhesive, or other thermosettable or crosslinkable curable resin, the level of external forces applied to a composite system or article having the composite system incorporated therein, the amount or quality of adhesion of adhesive composite system on an article, the thermal history of the composite system, etc.

The particular property measured will depend upon the detectable particles utilized/incorporated in the composite system. Particles exhibiting electromagnetic properties can have this property exploited to perform the desired measurements. For example, certain metals can scatter x-rays sufficiently, so x-ray transmission measurements can be used to quantify the amount of such particles within a material, which in turn can be used to determine, e.g., whether the proper amount of a two part adhesive has been applied.

If the particles have sufficiently high dielectric constant they will increase the dielectric constant of the curable resin into which they are incorporated in an amount related to the particle loading. The dielectric constant of the particles/functional groups can be determined by measuring the capacitance of a parallel plate capacitor containing the particles.

Microwave or inductive heating methods can also be used to heat the particles, after which the associated infrared emissions can be measured to quantify the amount of detectable particles in the curable resin, and thus, e.g., the amount of a part of a two part adhesive.

If the detectable component exhibits magnetic properties, magnetic permeability may be determined, typically via a measurement of inductance or inductive reactance, and used as an indicator of the level of stress within or applied to the resin system. Magnetic permeability is defined as the ratio of the total magnetic flux density in a sample to the externally applied magnetic field, and as such, will be a function of the number of magnetic particles within the resin system.

The particular method of measurement will depend upon the detectable property desirably being measured. Methods of measuring the detectable properties are known, and generally include thermometers or thermocouples for the measurement of thermal conductivity, magnetometers such as hall-effect sensors, giant magneto-resistive sensors, anisotropic magneto-resistive sensors, atomic magnetometers, superconducting quantum interference devices (SQUIDS) or eddy current coils for the measurement of magnetic permeability, capacitive plates or striplines for the measurement of dielectric constant, ohmmeters and eddy current coils for the measurement of electric conductivity, densitometers, ultrasound or x-ray for the measurement of density, magnetometers (as mentioned above) and coils for the measurement of nuclear quadruple resonance frequency. In those embodiments wherein the detectable particles comprise a ferromagnetic material, the sensors or array of sensors may desirably comprise, e.g., radiofrequency (RF) coils, with the appropriate driving instrumentations to measure the composite systems' material properties distribution.

Whatever the measurement method desired, appropriate sensors, or arrays of sensors, therefore are desirably operatively disposed relative to the article into which the composite system is desirably incorporated. In some embodiments, the sensor or array(s) of sensors may advantageously be attached to the article in close proximity to where the composite system is desirably applied. For example, in those embodiments where the composite system is used to bond parts of an article together, the sensors and/or array(s) of sensors may be mounted on a surface adjacent to the bond.

If desired, and depending on the measurement being taken, one or more transmitters could be utilized with the sensors/arrays so that enhanced detection capabilities and/or penetration depth is/are provided. It may also prove advantageous to actively excite the detectable particles with an external source (e.g., mechanical vibration or electromagnetic excitation) to alter their properties in a way that further reflects the structural integrity of the curable resin.

To conduct the nondestructive testing method of the present invention, the selected curable resin and plurality of detectable particles are combined to provide a composite system. The composite system would be applied to the desired article, typically in a fashion such as to bond two parts of the article, and sensors and/or sensor arrays operatively disposed relative thereto. Measurements may be taken by the sensors/sensor arrays while the composite system is applied, being cured, after curing, or during use of the article to which the composite system is applied. The measurements are conveniently relayed to data processing and/or image display components that enable real-time detection of defects, e.g., voids, porosity, cracks, etc., in the composite system. The results may advantageously be presented such that they are easily interpreted by non-NDT experts. This interpretation, in turn, may be used to alter the properties of the composite system, the application of the composite system, the conditions under which the composite system is being applied, or any other parameters capable of impacting the integrity of the cured composite system.

One embodiment of a nondestructive testing method can be further understood with reference to FIG. 2. As discussed above, FIG. 2 shows article 200 comprising first part 203 and second part 204 having composite system 201 interspersed therebetween. Sensor 205 is operatively disposed relative to composite system 201, and may receive signals from the detectable component therein while composite system 201 is applied or curing, or during use of article 200 indicative of the level of stress within composite system 201, the ratio of parts within composite system 201 in those embodiments wherein composite system 201 comprises a multi-part adhesive, etc. In FIG. 2, void 206 is depicted, which would be detected by sensor 205. Signals received by sensor 205 would desirably be relayed to data processing and/or image display components that enable real-time detection of defects, e.g., voids (such as void 206), porosity, cracks, etc., in composite system 204.

Although the composite system and method of the present invention are expected to find utility in a wide variety of applications, they are expected to be particularly advantageously applied in areas wherein assembly of parts is desirably carried out on site, so that shipping completely assembled articles can be avoided. Examples of industries wherein this capability may be advantageous include the energy industry, where large segments of, e.g., pipeline or other plant apparatus, are desirably shipped rather than the actual length or complete part to be utilized. One other example in the energy industry would be in the wind energy industry, wherein wind blades, or other parts of wind energy apparatus, may desirably be shipped in parts. Wind blade spar cap scarf joints may desirably be assembled/completed in the field, and the ability to confirm the integrity thereof advantageous. The method of the present invention would provide this capability as well as the capability to conduct in-service inspection of the wind blade leading edge, trailing edge, and shear web joints, as well as critical composite regions of the wind blade, such as root section, the spar cap, and tip. The method of the present invention would also allow for the structural health monitoring of wind blades, via the permanent mounting of the sensors or arrays of sensors on the wind blade during field assembly.

In certain embodiments, the present invention desirably provides the advantage of being capable of providing in-situ monitoring of the composite system, either while being applied, during curing, after curing, and/or during use of the article to which the composite system is applied. In such embodiments, and when the detectable materials comprise a conductive or ferromagnetic material, in-situ monitoring of the composite system may typically be accomplished by conductivity or magnetic permeability measurement, which could be done using eddy current sensors.

More particularly, eddy current sensors can be used to detect magnetic fields from eddy currents induced in the composite system. In the presence of a flaw, the eddy currents and the corresponding magnetic fields would be disturbed, which results in a change in the sensor response indicating the flaw. When large articles are being bonded, anti-parallel (also known as meandering) drive coils may be utilized as these are capable of producing a drive field and the corresponding eddy current in a large area. However, since current flows in opposite directions in adjacent lines, the field/eddy currents may not penetrate deeply into the article/composite system and detection may be limited to flaws substantially at, or close to, the surface.

Figure 3A:
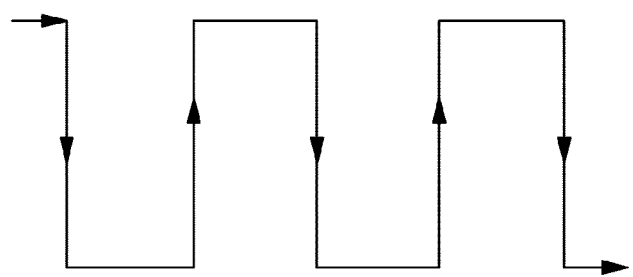
FIG. 3A is a schematic view of an anti-parallel drive.
Figure 3B:
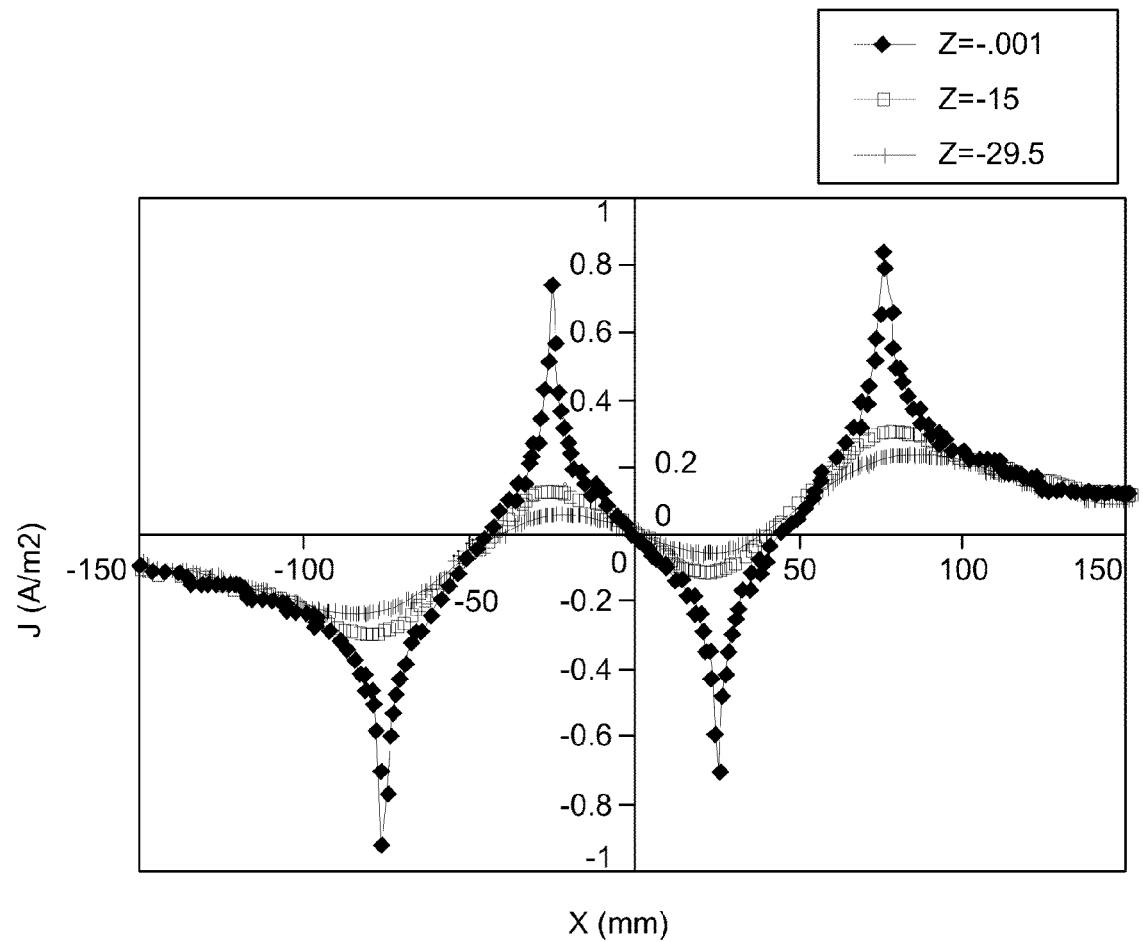
FIG. 3B is a graph depicting the typical current density at different depths for the anti-parallel drive shown in FIG. 3A.
Figure 3C:
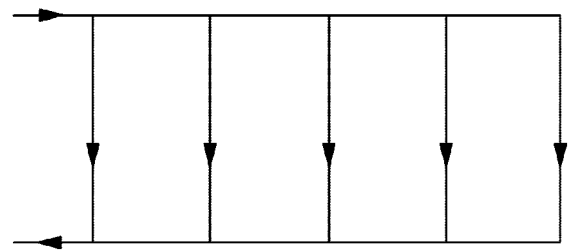
FIG. 3C is a schematic view of a parallel drive.
Figure 3D:
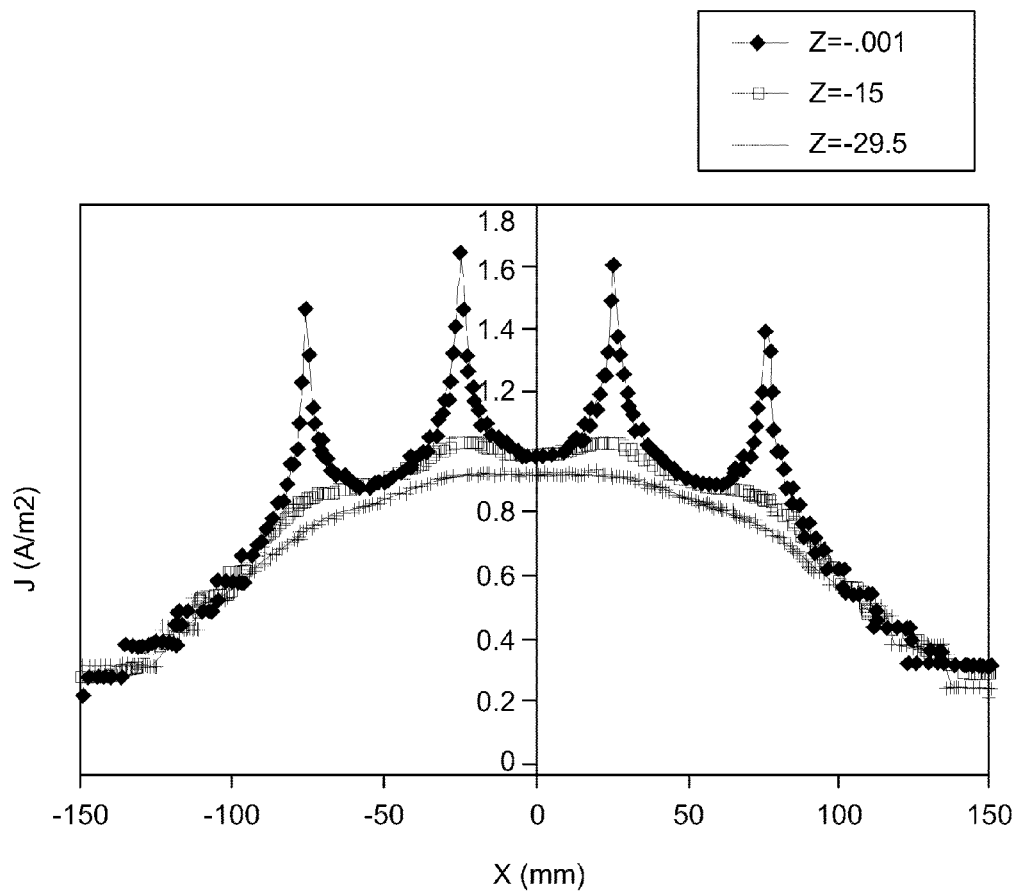
FIG. 3D is a graph depicting the typical current density at different depths for the parallel drive shown in FIG. 3D.

In order to overcome this problem, eddy current sensors utilized to detect the detectable component in certain embodiments of the invention may have the drive lines arranged in parallel (as shown in FIG. 3C), which results in much higher fields and much deeper penetration as compared to the anti-parallel drive lines (shown in FIG. 3A). FIG. 3 shows the current density at different depths of penetration for anti-parallel (FIG. 3B) and parallel drives (FIG. 3D), for the same current flowing through each of the parallel lines as well as in the anti-parallel drive line for a simple case of four lines. It can be seen that not only is the peak current density higher with the parallel lines, the decay is much slower with the parallel drives. In addition, at larger depths, the current density gets more uniform with the parallel drive excitation.

A basic configuration for the array probe would be a set of parallel drive lines and an array of sense (or receive) coils between the drive lines. However, the response of the sense coil to a flaw depends on where the flaw is with respect to the drive and the sense coil. If for instance, there is a 1-D array of sense coils between two adjacent drive lines, and if a flaw happens to be centered approximately below the sense coil, it will have a very low response since the voltage induced in the sense coil tends to cancel out. These areas are referred to as blind zones since a flaw can potentially be missed in this region. Blind zones will exist even if the sense coil is placed on top of the drive lines instead of between the drive lines.

Figure 4A:
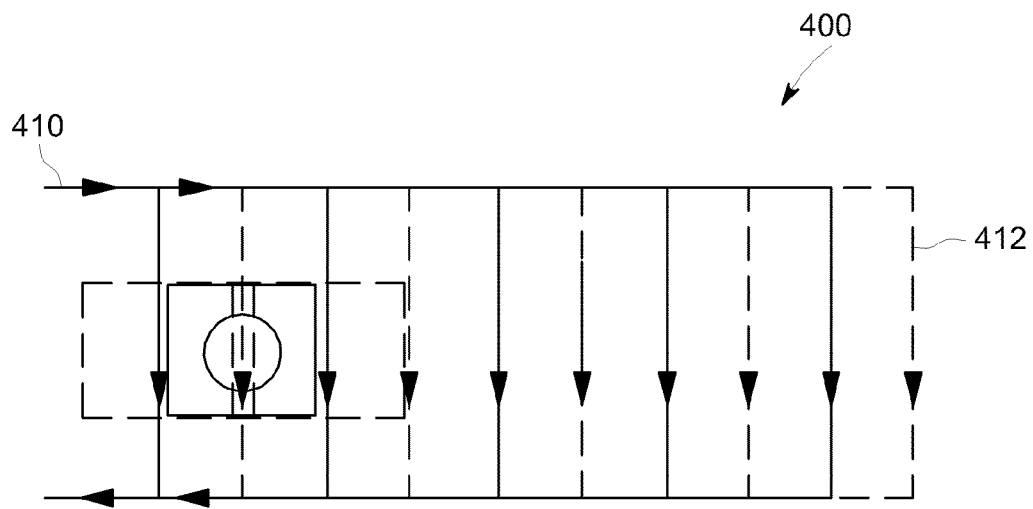
FIG. 4A is a top, schematic view an eddy current array probe according to one embodiment, comprising two offset layers.

In order to ensure that flaws at any location are detected with reasonable signal levels, one embodiment of an array probe useful in the present method may include a second layer of drive lines and sense coils, identical to the first layer, but offset from the first layer, to enable a null response from one sense coil to be compensated by a high response from two sense coils in the adjacent layer. Array probes used in the method may also have more than 2 layers, in which case the layers will be offset accordingly. FIG. 4 shows one such embodiment of array 400. Alternately if space is not a constraint and the array is scanned, instead of multiple layers, there can be two or more rows of drive and sense elements, offset from each other.

Figure 4B:
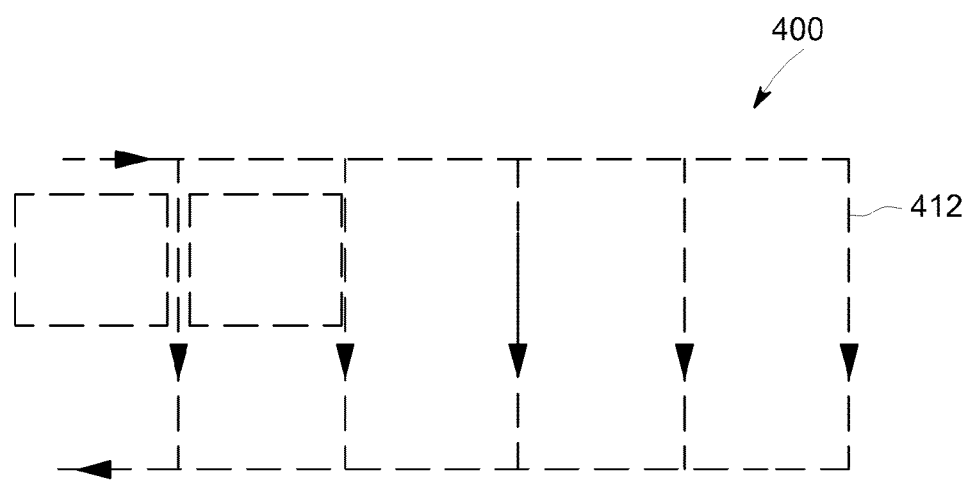
FIG. 4B is a top, schematic view of only one layer of the two layer eddy current array probe shown in FIG. 4A.

As mentioned earlier, the response from the same flaw at a constant depth can be very different based on the location of the flaw with respect to the drive lines and sense coil. Desirably, this response would be flat, i.e., a constant response would be provided regardless of the location of the flaw. In the design shown in FIG. 4A, the response from the sense coils in the two layers 410 and 412, can be combined to give a compensated response that is reasonably flat, i.e., the compensated response will no longer be dependent on the location of the flaw. For purposes of clarity of illustration, FIG. 4B shows only one layer, 412.

Figure 5:
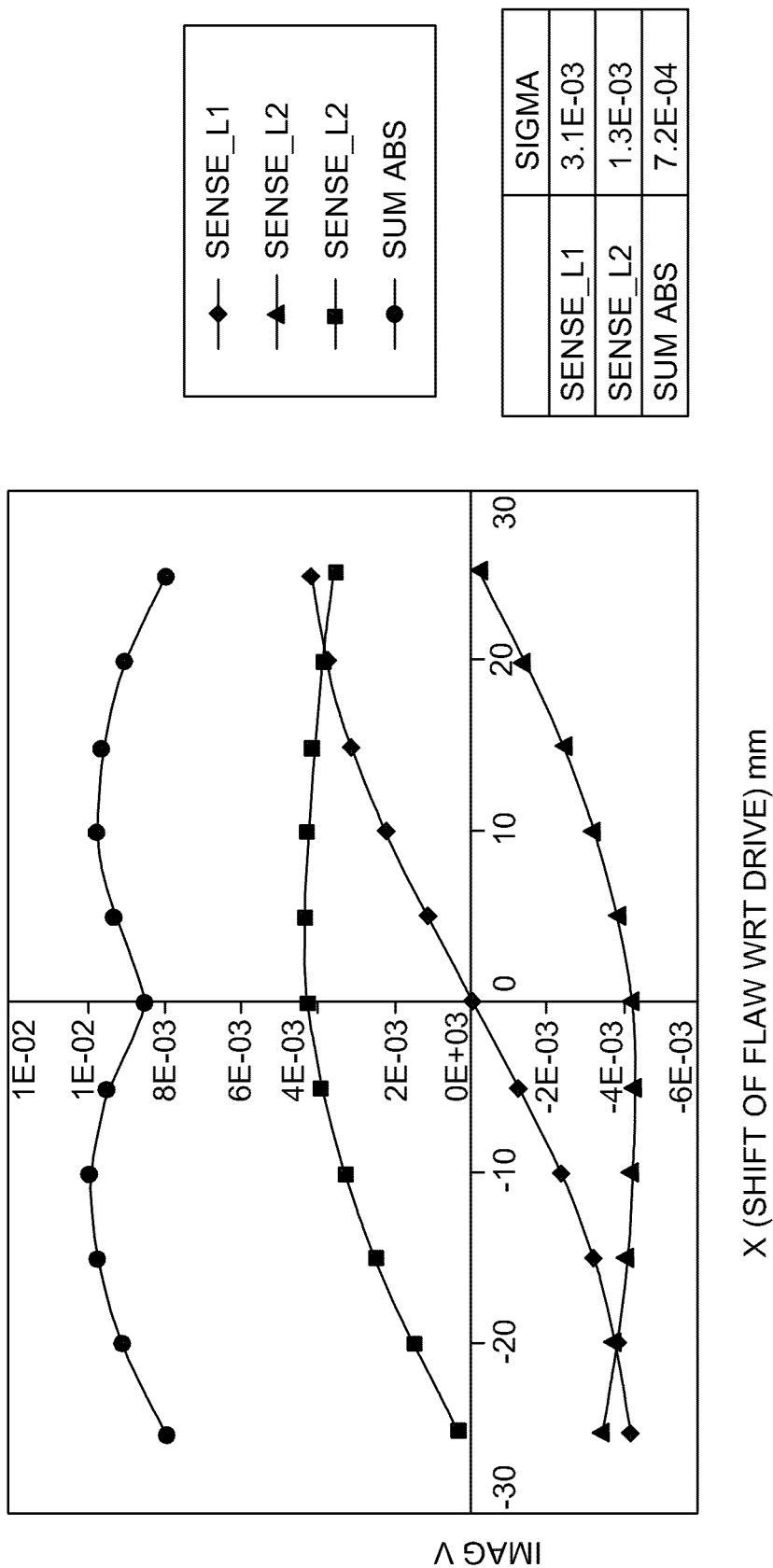
FIG. 5 is a graph showing the response from the individual sense elements, as well as a combined response from three sense coils, of the array shown in FIG. 4.

FIG. 5 shows the response from the individual sense elements of array 400 as well as the compensated (combined) response from the three closest sense coils. This compensated response is the Sum of the absolute value (Sum_Abs) of the three sense coils at each location. The table shows the standard deviation of the response to a flaw for each sense coil as well as for the compensated response. It may be seen that the sigma of the compensated response is significantly lower than that of the individual coils. Compensation may be achieved by alternate means of combining the signals as well.

In one particular exemplary application of the present method, a system of eddy current (EC) arrays may be utilized to detect the detectable particles, where the array consists of a drive in the form of a single or multiple current loops and a linear one dimensional (1-D) array of one of more sense coils between adjacent drive lines. In this embodiment, the drive would be connected directly to the eddy current instrument, while the array of coils would be connected to a multiplexer circuit that connects them to the eddy current instrument. The EC array would then be placed on the outside surface of the jointed structures desirably bonded with the composite system. For example, in the wind blade, this could be a scarf joint of the spar cap, the double strap joint of the shearweb, or the butt joint of the skin. The array would also be connected to an encoder to register as the surface is scanned. The scan may be done manually, or may be motorized. The desired composite system would be prepared, e.g., comprising an adhesive as the curable resin and ferrite particles. The particle size, surface treatment, and volume fraction may advantageously be selected to be sufficient to produce a detectable signal as well as to maintain the adhesive's chemical and physical properties, e.g., viscosity, cure rate, post cure Young modulus, ultimate shear strength, fatigue strength, shelf-life, etc, or combinations of these. The scan may be performed as the composite system is being injected, after it is injected, during curing, after curing, after rework, or in-service. The data collected from the array of coils and the encoder is processed to form 2-D images of the distribution of the composite system within the bond space.

Alternately, the eddy current array may consist of a drive in the form of single or multiple current loops and a two dimensional (2-D) array of sense coils between two adjacent drive lines. The array would be used to scan and generate images for the composite system as it is being injected, after it is injected, during curing, after curing, after rework, or in-service as described above.

In a further embodiment, the eddy current array with either 1-D or 2-D array or sense coils between adjacent drive lines, can be provided being of the full size of the inspection area such that it generates images without the need for manual or motorized scanning. The drive lines can be multi-turn to increase the eddy current density and the signal level.

Figure 6:
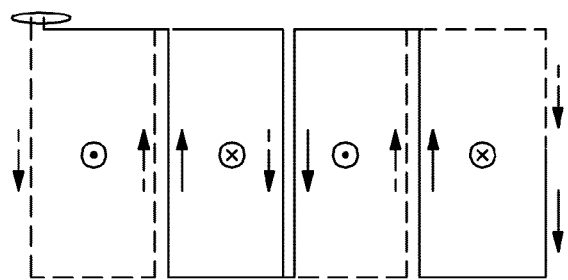
FIG. 6 is a schematic view of an eddy current array probe according to an additional embodiment.

FIG. 6 illustrates an array probe useful in the present method having an anti-parallel drive configuration wherein the drive line is setup in a multiple turn and multilayer format that enables alternating magnetic flux directions between two adjacent set of drive lines. This configuration does produce lower net flux than the parallel case, but still allows for considerable improvement in depth of penetration over the circular drive coils used in conventional EC probes.

Figure 7A:
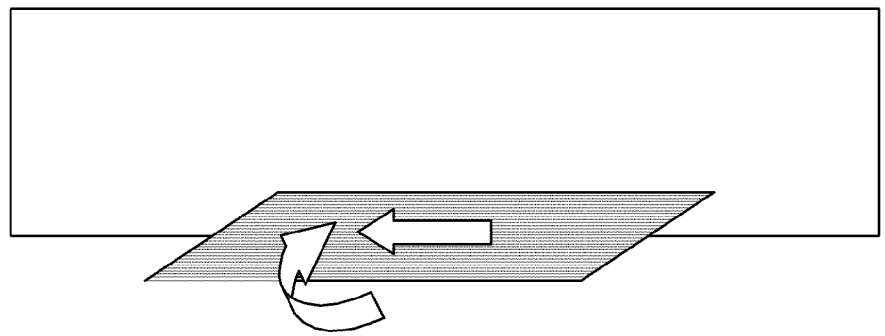
FIG. 7A is a schematic view of one embodiment of an eddy current array probe wherein the return path is orthogonal to a drive coil, so that a magnetic flux is parallel to one produced by the drive.
Figure 7B:
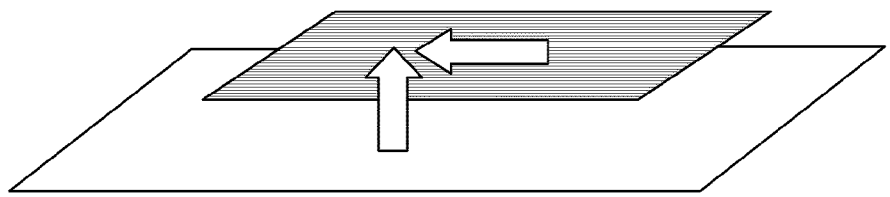
FIG. 7B is a schematic view of one embodiment of an eddy current array probe wherein the return path is in the drive coil plane.

If a parallel drive is to be used in the current array probe, the return path to complete the loop must be in a plane that is orthogonal to the plane of the drive coil (as shown in FIGS. 7A and 7B), otherwise the whole structure acts like a circular loop (unless the loop is then made very large compared to the area of the parallel drive region). Anti-parallel loops, on the other hand, lend themselves quite well to use in situations where space is tight, as may be the case with joints within a wind blade, e.g., the shear web joint. Array probes with anti-parallel drive lines may also have multiple layers/rows with drive and sense offset to avoid any blind zones and to get a flat compensated response.

In some embodiments, a drive coil can be used to generate a uniform field and/or to increase depth penetration possible with the drive. In such embodiments, the drive coil may desirably comprise a current density that monotonically increases from the center of the coil to an outer edge of the coil. The current density may be increased by increasing current and/or increasing turn density. The coil may, in some embodiments, comprise from about 5 to about 100 turns. In some embodiments the drive coil may advantageously comprise a spiral drive coil. In some embodiments of such a spiral drive coil, the coil may have a current density given by the equation $\ln(1+k*n)$, where r is the distance from the center of the coil, n is the turn number, and k is between about 0.05 and 3, or from about 0.1 and 2. It is known to those skilled in the art that turn density of a coil is defined as the number of turns per unit length of the coil. In other words, the turn density and the turn number are directly proportional to each other; i.e., the higher turns per unit diameter results in higher turn density. Conventional coils have uniform turn density, which means that regardless of the distance from the center, the number of turns per unit length stays the same. On the hand, in the coil of the invention, the turn density increases as a function of distance (or unit length) from the center, unlike conventional coils.

In some embodiments, the drive coil may be provided in combination with a sensor, or plurality of sensors, to provide a measurement probe. The probe can generate 2-D images without the problems that can be associated with single point or raster scanned measurement probes. For example, in order to create 2D information from a single point measurement system, multiple measurements must be taken and assembled to create the 2-D image, and with raster scanned measurements, individual left to right scans typically must be combined in order to do so.

The sensor or plurality of sensors may desirably be provided in connection with a surface, separated from a surface comprising at least a portion of the drive coil by a distance of from about 0 mm to about 25 mm. In some embodiments, the drive coil is desirably flat, so that substantially the entirety of the same lies within the same drive coil surface. In other embodiments, the drive coil may be curved. In such embodiments the distance between the sensing plane and the drive coil plane is desirably measured at or near a horizontal axis running through both the sensing plane and the drive coil plane. In those embodiments wherein the measurement probe comprises a plurality of sensors, the sensors may be arranged in any configuration within the sensing surface. In some embodiments, the sensors are arranged as an array.

Figure 14:
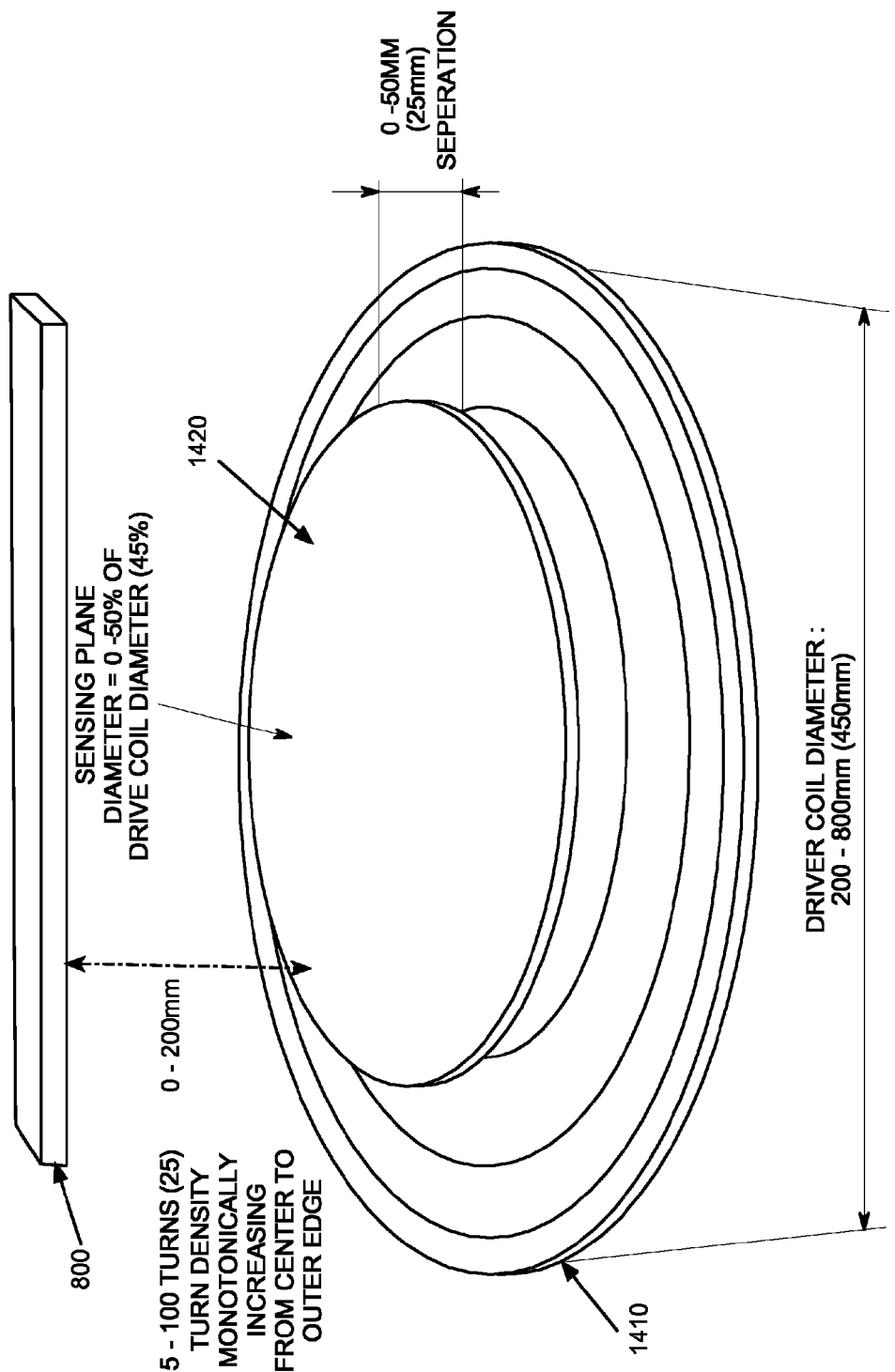
FIG. 14 is a schematic representation of one embodiment of a measurement probe comprising a spiral drive coil and a sensing plane.

One embodiment of a measurement probe comprising a spiral drive coil 1410 is shown in FIG. 14. As shown in FIG. 14, drive coil 1410 is substantially flat and substantially the entirety of drive coil 1410 lies within a drive coil surface (not shown). As discussed above, this is not necessarily the case, and drive coil 1410 may be curved, if desired. Drive coil 1410 comprises a current density that monotonically increases from the center of drive coil 1410 to an outer edge of drive coil 1410. In the embodiment shown in FIG. 14, the increase in current density is provided by the turn density of drive coil 1410.

Sensing surface 1420 is provided and is disposed at a distance of from about 0 mm to about 25 mm from drive coil 1420 and is substantially parallel thereto. Sensing surface 1420 comprises at least one sensor, a plurality of sensors, which in some embodiments, may be arranged in an array.

Figure 8:
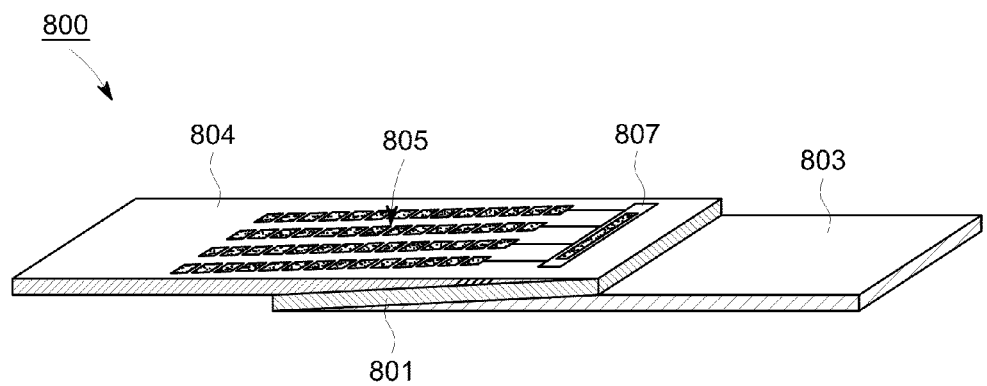
FIG. 8 is a schematic view of a further embodiment of the present article.

An article according to one embodiment is shown in FIG. 8. As shown, article 800 comprises first part 803 and second part 804, with composite system 801 interspersed therebetween. First part 803, second part 804 or both may comprise a carbon composite. Composite system 801 may desirably comprise an adhesive as the curable resin, and ferrite powder as the detectable particles. Sensor 805, in this embodiment, an array, is operatively disposed relative to composite system 801, and may receive signals from the detectable particles therein while composite system 801 is applied or curing, or during use of article 800. Signals received by sensor array 805 would desirably be relayed to data processing and/or image display components that enable real-time detection of defects via instrument interface 807.

Any of the aforementioned arrays may, if desired, be operatively disposed on the inside surfaces (i.e., bonding surfaces) of the parts of the article to be bonded, such that the array is closer to the composite system. In such embodiments, the arrays will desirably be fabricated on a thin substrate and comprised of a material that will bond sufficiently to the inner surface of the structure as well as to the composite system so that an extraneous defect will not be introduced into the composite system.

Additionally, any of the aforementioned arrays may be disposed within any layers of the article to be bonded. For example, the articles to be bonded can be glass fiber or carbon fiber composites. The array may then be a printed circuit of a thin film polyimide that is placed between the layers of composites during lay-up or on the inside surfaces (i.e., the bonding surfaces) of the structures and then covered with an extra layer of the same material of the structure, or with a different materials that can enhance the bonding between the array and the adhesive.

Of course, in any of the aforementioned examples, alternative detectable particles, measurable with the aforementioned eddy current probe, could be utilized.

Any of the above embodiments may also be applied to the inspection of the flow of the composite system through the composite fibers, for example, in Vacuum Assisted Resin Transfer Molding or Resin Transfer Molding processes. In such embodiments, the curable resin may desirably comprise detectable particles of specific size, shape, and surface treatment e.g., silane or other coupling agent. Such embodiments of the present method may desirably be applied to inspect wind blade glass or carbon composite parts, like the blade root pre-fabricated section, spar cap, leading edge, trailing edge, tip, or core.

Example 1

Figure 9:
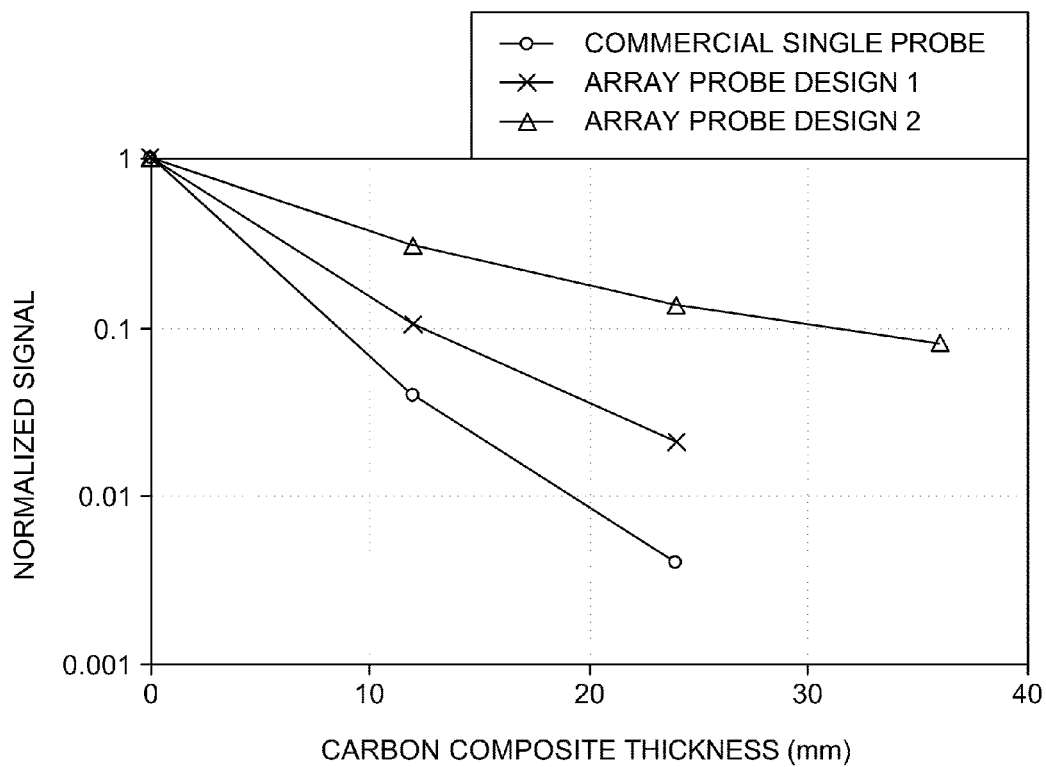
FIG. 9 is a graph depicting the results obtained from the measurement of the eddy current signal obtained from an article similar to that shown in FIG. 8 using a conventional circular probe, a parallel drive with the conventional probe as the sense probe, and an anti-parallel drive with the conventional probe as the sense probe.

A composite system according to one embodiment, comprising an adhesive as the curable resin, and ferrite powder, TSF-50ALL, from TSC International, as the plurality of detectable particles, with a ratio of 9:1 adhesive to ferrite by weight was used to bond samples of carbon composite materials. The article(s) 800 so produced is/are similar to that shown in FIG. 8, and comprise first part 803 and second part 804, with composite system 801 interspersed therebetween. Second part 804 comprised carbon composite material, and was prepared in varying thicknesses. FIG. 9 shows experimental results obtained from the measurement of the eddy current signal from articles 800 each comprising a second part 804 of differing thickness using a conventional circular probe, a parallel drive with the conventional probe as the sense probe (Design 2 in FIG. 9), and an anti-parallel drive with the conventional probe as the sense probe (Design 1 in FIG. 9). A conventional probe was used as the sense element for all measurements, for comparison purposes.

Example 2

Figure 10:
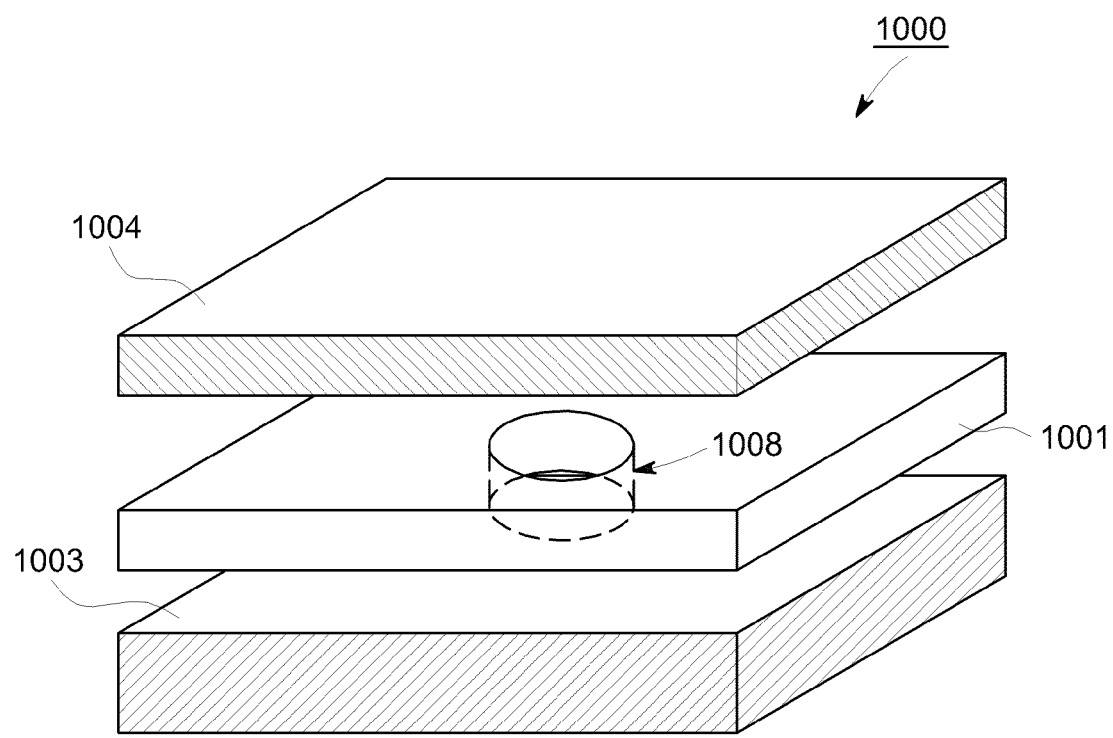
FIG. 10 is a schematic view of an additional embodiment of the present article.

A composite system according to one embodiment, comprising an adhesive as the curable resin, and ferrite powder, TSF-50ALL, from TSC International, as the plurality of detectable particles, was used to bond samples of carbon composite materials. The article 1000 so produced is shown in FIG. 10, and comprises first part 1003, second part 1004, with composite system 1001 interspersed therebetween. First and second parts 1003 and 1004 may advantageously comprise carbon composite material. Artificial voids were introduced within composite system 1001 by placement of a 1.5" plastic disk 1008 within composite system 1001 during application thereof.

Figure 11A:
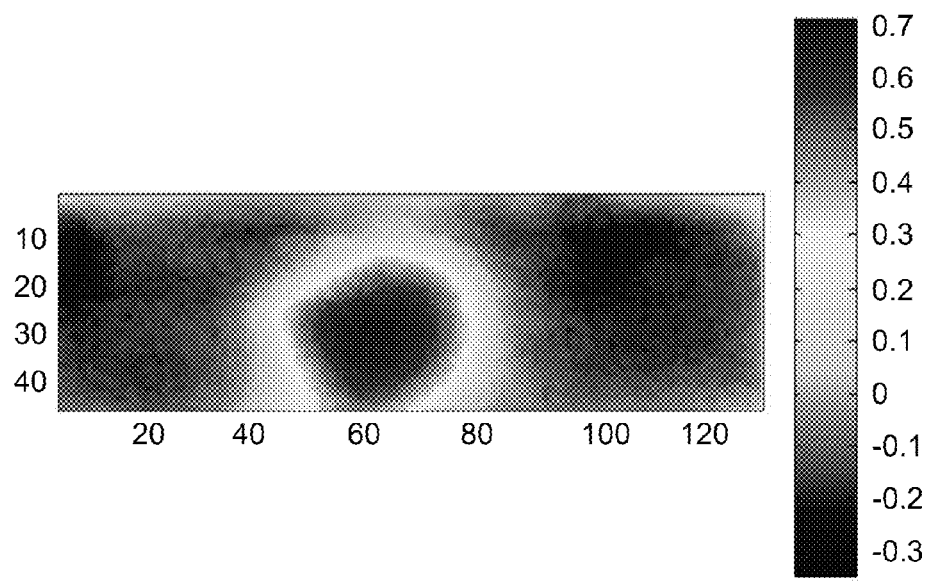
FIG. 11A is the eddy current scan image for the article shown in FIG. 10, when the composite system comprises a ratio of 9:1 of the curable resin to the detectable component, by weight.
Figure 11B:
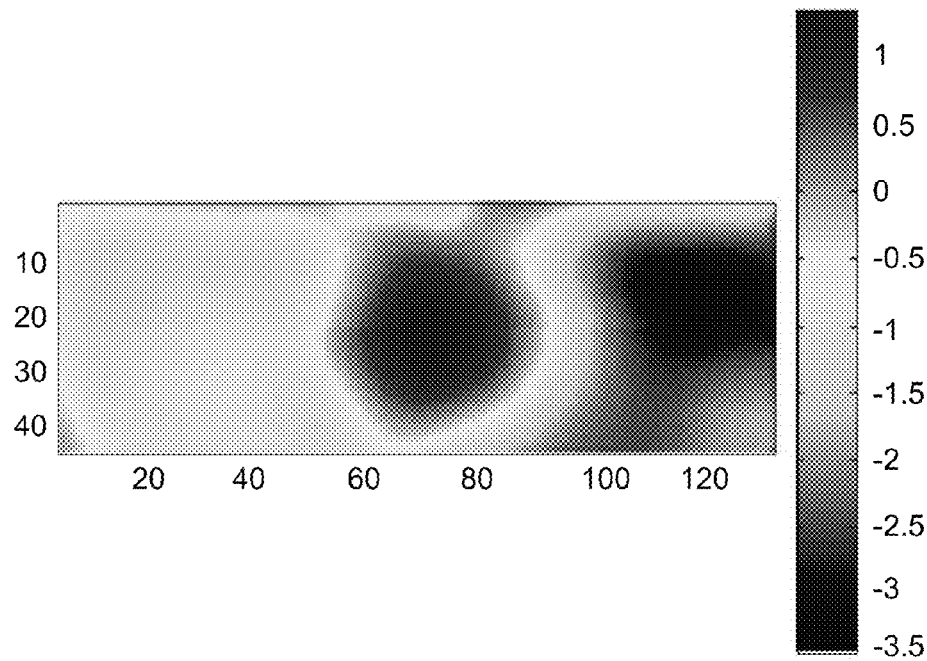
FIG. 11B is the eddy current scan image for the article shown in FIG. 10, when the composite system comprises a ratio of 9:2 of the curable resin to the detectable component, by weight.

After curing, the samples were scanned with the Eddy Current probe, 700P24A4, from GE Inspection Technologies. The experiments were done on 2 samples of different mixing ratio of the adhesive and the ferrite powder, namely 9 to 1 and 9 to 2 adhesive to ferrite powder by mass. The results of this experiment are shown in FIG. 11A and FIG. 11B, respectively. As shown, at both concentrations of detectable particles, the void induced by the introduction of plastic disc 1008, is readily and easily observed.

Example 3

A composite system according to one embodiment, comprising an adhesive as the curable resin and ferrite powder as the plurality of detectable particles was prepared and utilized in an article comprising an electrically conductive material, e.g., carbon composite, according to a further embodiment.

Figure 12A:
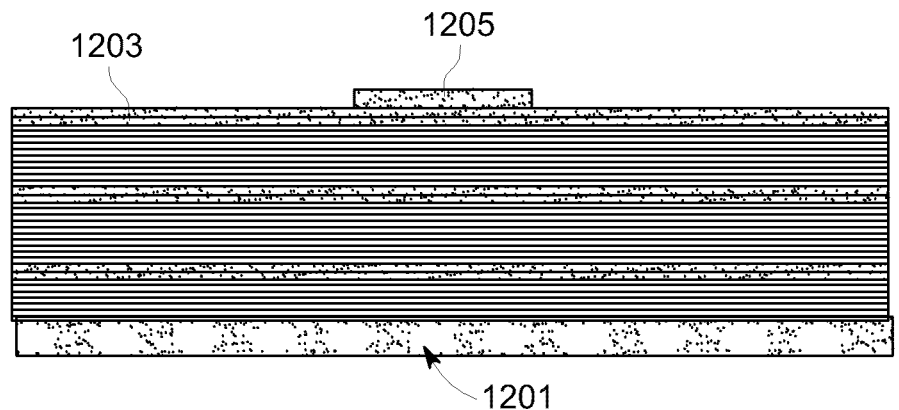
FIG. 12A shows an additional embodiment of the present article, comprising only a first part, further comprised of electrically conductive material.
Figure 12B:
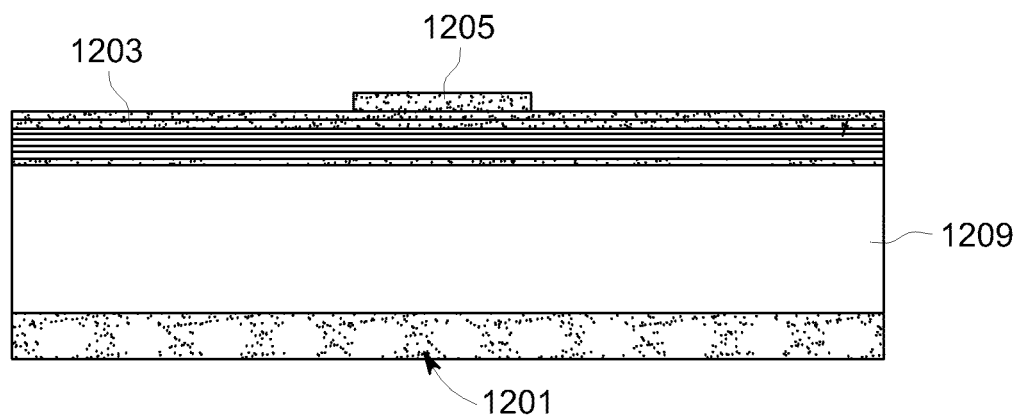
FIG. 12B shows an additional embodiment of the present article, comprising only a first part, further comprised of electrically conductive material, with an air gap disposed between the first part and the composite system.

As shown in FIG. 12A, for one sample, first part 1203 was 35 mm thick and composite system 1201 was applied directly thereto. For the second sample, shown in FIG. 12B, a first part 1203 with a thickness of 5 mm was disposed relative to composite system 1201 with a 30 mm air gap 1209 therebetween. For both samples, sensor 1205 was placed on a surface of first part 1203 opposite to composite system 1201.

Figure 13A:
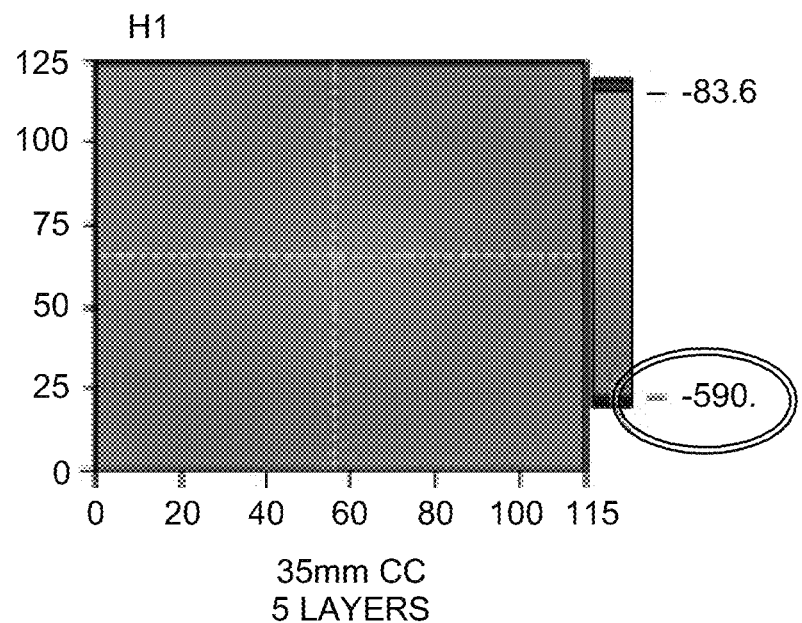
FIG. 13A is the eddy current scan image for the article shown in FIG. 12A.
Figure 13B:
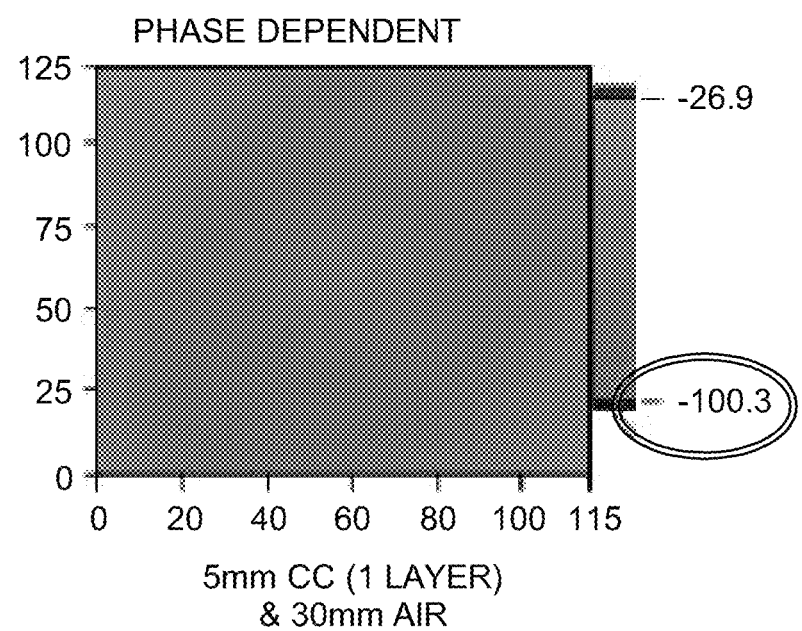
FIG. 13B is the eddy current scan image for the article shown in FIG. 12B.

FIG. 13 shows the eddy current signal of a conventional eddy current probe with 5-mm and 35-mm carbon composite between the sensor and the ferrite-adhesive composite to be inspected. As shown, the signal provided by the 35-mm carbon composite is greater than that provided by the 5 mm carbon composite with a 30 mm air gap, illustrating that electrically conductive components may be utilized in the articles described herein, and rather than resulting in a lowered sensitivity when measured according to the present method, actually provide enhanced signals.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A measurement probe, comprising:
   a spiral drive coil having a current density that monotonically increases from a center of the drive coil to an outer edge of the drive coil;
   a sensing surface disposed at a distance from the drive coil, the sensing surface parallel to the drive coil and comprising at least one sensor; and
   an article comprising a first part, a second part and a composite system disposed at a distance from the sensing surface, the composite system comprising a curable resin and a plurality of detectable particles, the at least one sensor receiving signals from the plurality of detectable particles.

2. The measurement probe of claim 1, wherein the distance is in a range between about 0.5 mm to about 25 mm.

3. The measurement probe of claim 1, wherein the drive coil has a coil diameter of from about 200 mm to about 800 mm.

4. The measurement probe of claim 3, wherein the sensing surface has a diameter in a range between about 0.1-50% of the coil diameter.

5. The drive coil of claim 1, wherein the drive coil comprises from about 5 to about 100 turns.

6. The measurement probe of claim 1, wherein the first and second parts of the article comprises carbon composite material.

7. The measurement probe of claim 1, wherein the at least one sensor comprises a sensor array that receives signals from the plurality of detectable particles.

8. The measurement probe of claim 7, further comprising an instrument interface for receiving signals from the sensor array for enabling real-time detection of defects.

* * * * *